United States Patent [19]
Dembinski et al.

[11] Patent Number: 5,136,021
[45] Date of Patent: Aug. 4, 1992

[54] TNF-INHIBITORY PROTEIN AND A METHOD OF PRODUCTION

[75] Inventors: Wlodzimierez E. Dembinski, Buffalo; Margot Ip, Orchard Park, both of N.Y.

[73] Assignee: Health Research, Inc., Buffalo, N.Y.

[21] Appl. No.: 486,044

[22] Filed: Feb. 27, 1990

[51] Int. Cl.$^5$ .............................................. C07K 15/00
[52] U.S. Cl. ................................. 530/350; 530/351; 530/369
[58] Field of Search ................... 530/350, 351, 369

[56] References Cited

PUBLICATIONS

Lin et al. Immunology 63 pp. 663–668 (1988).
Kamijo et al. Biochem. Biophys. Res. Comm. 158(1) pp. 155–162 (1989).
Purification and initial characterization of a type βtransforming growth factor from human placenta Charles A. Frolik et al. Proc. Natl. Acad. Sci. USA, 80: 3676–3680, 1983.
A Tumor Necrosis Factor-binding Protein Purified to Homogeneity from Human Urine, Protects Cells from Tumor Necrosis Factor Toxicity/Hartmut Engelmann et al. J. Biol. Chem. 264: 11974–11980, 1989.
Purification and Biologic Characterization of a Specific Tumor Necrosis Factor a Inhibitor Philippe Seckinger et al. J. Bio. Chem., 264: 11966–11973, 1989.
A Tumor Necrosis Factor Binding Protein is present in human biological fluids Christina Peetre et al., Eur. J. Haem., 41: 414–419, 1988.
Philippe Seckinger et al. J. Biol. Chem. 264: 11966–11973, 1989.
A Tumor Necrosis Factor Binding Protein is present in human biological fluids, Christina Peetre, et al. Eur. J. Haem., 41:414–419, 1988.

Primary Examiner—David L. Lacey
Assistant Examiner—Shelly J. Guest
Attorney, Agent, or Firm—Pennie & Edmonds

[57] ABSTRACT

A TNF-inhibitory protein having a molecular weight of 28 kilodaltons and having an activity of rendering resistant to TNF a TNF- sensitive cell to thereby inhibit the cytolytic and/or cytostatic activity of TNF for the TNF-sensitive cells and a method for producing the same are described. The TNF-inhibitory protein can advantageously be used as an antigen for producing an antibody useful for detecting a patient having TNF-resistant cancer and for removing the TNF-resistance of the cancer cells of the patient.

12 Claims, 2 Drawing Sheets

TNF-INHIBITORY PROTEIN AND A METHOD OF PRODUCTION

TABLE OF CONTENTS

Background Of The Invention
Technical Field
Background Art
Summary Of The Invention
Brief Description Of The Drawings
Detailed Description Of the Invention
Description Of Preferred Embodiments
Example 1
Example 2
Example 3
Claims

Background Of The Invention

Technical Field

This invention relates to a proteinaceous substance which inhibits the cytolytic and/or cytostatic activity of tumor necrosis factor (hereinafter referred to as "TNF") for a TNF-sensitive cell, and a method for producing the same. The proteinaceous substance of the present invention, which is designated herein as "TNF-inhibitory protein" ("TIP"), can advantageously be used as an antigen for producing an antibody which is not only useful for identifying patients with cancers that are resistant to the cytolytic activity of TNF, but also useful for removing the TNF resistance of the cancers of such patients.

Background Art

TNF, a protein having multifaceted biological activities affecting cell growth, such as differentiation and proliferation, is well-known for its antitumor necrotic activity. Numerous in vitro experiments have shown that TNF is a potent, cytolytic and/or cytostatic agent against many types of tumor cell lines.

Many clinical trials have been conducted on TNF as a therapeutic agent for treatment against tumors. However, results of early clinical trials have been disappointing because tumors often do not respond to treatment with TNF, or after partial tumor remission following TNF treatment, patients become resistant to further treatment with TNF. This development of resistance to the cytocidal activity of TNF restricts the use of TNF for the treatment of tumors.

Recently, proteins having an inhibitory activity against the cytocidal activity of TNF have been reported (J. Biol. Chem., 264: 11974–11980, 1989; J. Biol. Chem., 264: 11966–11973, 1989; Eur. J. Haem., 41: 414–419, 1988; Eur. J. Haem., 42: 270–275, 1989; and J. Biol. Chem., 265: 1531–1536, 1990). The reported proteins have been characterized as TNF binding proteins or TNF inhibitors, such as TNF α inhibitor. These proteins can directly inhibit the cytocidal activity of TNF when the proteins are added to TNF. On the other hand, there are reports suggesting that the treatment of a certain type of cell with TNF induces the production of a TNF-like protein, interleukin-1 (hereinafter referred to as "IL-1") or interleukin-6 (hereinafter referred to as "IL-6").

SUMMARY OF THE INVENTION

The present inventors have made extensive and intensive studies on the mechanism of resistance to TNF. As a result, they have unexpectedly found that when cells, such as cells of human fibroblast MLD or BG-9 or FS-4 cell lines, peripheral blood leukocytes or established tumor cells, are treated with specific inducers such as TNF, IL-1, IL-6, lymphotoxin, interferon-α and the like, those cells markedly produce a novel proteinaceous substance which causes the cells to be resistant to the cytolytic and/or cytostatic activity of TNF. The present inventors have succeeded isolating, purifying and identifying the substance. The substance was designated "TNF-inhibitory protein". It has also been found that the same substance as the TNF-inhibitory protein is formed in the serum of a patient suffering from cancer to whom TNF was administered. It has further been found that the TNF-inhibitory protein is advantageous for use as an antigen for producing an antibody specific therefor which is extremely useful not only for detecting a patient suffering from TNF-resistant cancer but also for removing the TNF resistance of the cancer of the patient. Based on these novel findings, the present invention has been completed. Accordingly, an object of the present invention is to provide a novel proteinaceous substance having TNF-inhibitory activity (TNF-inhibitory protein), which is useful for producing an antibody having the above-mentioned advantages.

Another object of the present invention is to provide a method for producing this novel TNF-inhibitory protein.

The foregoing and other objects, features and advantages of the present invention will be apparent to those skilled in the art from the following detailed description taken in connection with the accompanying drawings.

DETAILED DESCRIPTION OF THE INVENTION

Figure 1:
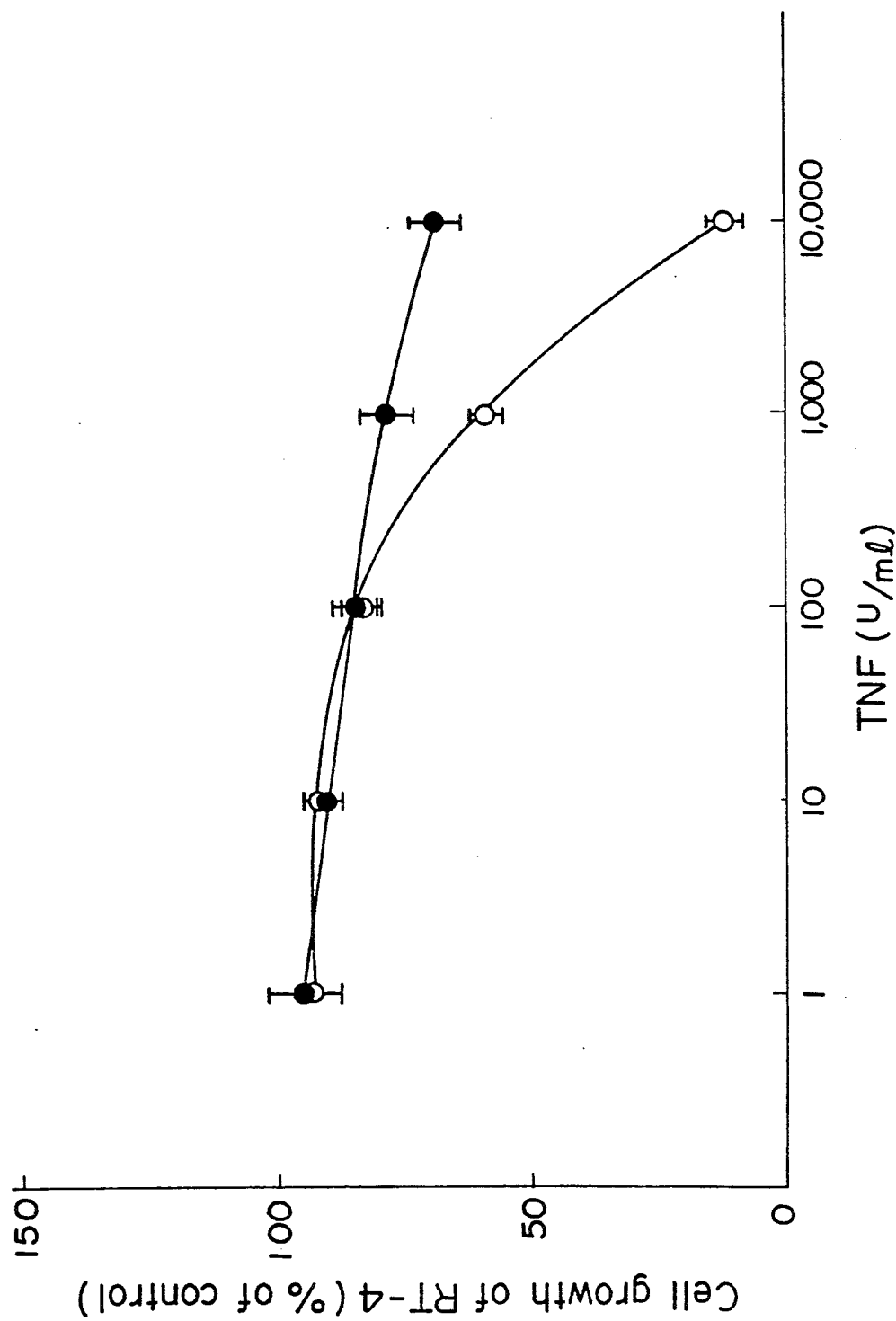
FIG. 1 is a graph showing the relationship between the concentration of TNF and the growth of RT4 cells (human bladder transitional-cell papilloma line) treated with the TNF-inhibitory protein (shown by the symbol "●—●", in comparison with the corresponding relationship for the case where the cells are not so treated (shown by the symbol "O—O"

According to the present invention, there is provided a TNF-inhibitory protein having:

(a) a molecular weight of 28 kilodaltons;

(b) no activity of directly inhibiting the activity of tumor necrosis factor; and (c) an activity of imparting TNF-resistance to a TNF-sensitive cell to thereby inhibit the cytolytic and/or cytostatic activity of said TNF in the TNF-sensitive cell.

The TNF-inhibitor of the present invention is a proteinaceous substance having a molecular weight of 28 kilodaltons (hereinafter referred to as "kDa") as measured by the customary method of sodium dodecyl sulfate-polyacrylamide gel electrophoresis (hereinafter referred to as "SDS-PAGE"), and an activity of imparting TNF-resistance to a TNF-sensitive cell to thereby inhibit the cytolytic and/or cytostatic activity of TNF for the TNF-sensitive cell. That is, when the TNF-sensitive cell has been treated with the TNF-inhibitory protein of the present invention, the cell is no longer influenced by the cytolytic and/or cytostatic activity of TNF. Examples of TNF-sensitive cells include cells of human fibroblast cell line MLD, human bladder transitional-cell papilloma line RT4, human ovarian carcinoma cell line A2780, and the like. In the case of MLD cells, the TNF-inhibitory protein of the present invention inhibits the cytolytic and/or cytostatic activity of TNF for MLD cell in the presence of cycloheximide (hereinafter referred to as "CHI").

The TNF-inhibitory protein of the present invention, does not directly inhibit the activity of TNF. That is, even when the TNF-inhibitory protein is incubated together with TNF, the activity of TNF is not lowered. Therefore, even when the incubated mixture has been added to a TNF-sensitive cell, the TNF still exhibits cytolytic and/or cytostatic activity.

The above-mentioned activity of the TNF-inhibitory protein in inhibiting the cytolytic and/or cytostatic activity of the present invention for a TNF-sensitive cell is not affected even when the TNF-inhibitory protein is incubated with monoclonal or polyclonal antibodies against TNF, IL-1 and IL-6.

The TNF-inhibitory protein of the present invention is a heat-labile protein.

The TNF-inhibitory protein may be modified according to the method for producing the TNF-inhibitory protein as in the case of a general protein. The TNF-inhibitory protein of the present invention includes all of such modified proteins as long as the modified proteins have the above-mentioned activities.

The TNF-inhibitory activity of the TNF-inhibitory protein of the present invention can be determined in terms of the ratio of survival of cells of human fibroblast cell line MLD after the cells treated with the TNF-inhibitory protein have been incubated together with TNF in the presence of cycloheximide, as described below.

The TNF-inhibitory protein of the present invention is completely different from the conventional TNF binding protein and TNF $\alpha$ inhibitor described above. The reasons therefor are as follows.

The mechanism of action of the TNF-inhibitory protein of the present invention appears to differ from those of the TNF binding protein and TNF $\alpha$ inhibitor. There are reports that the TNF-binding protein and the TNF $\alpha$ inhibitor block the function of TNF by binding to TNF and thus compete for TNF with a TNF receptor. On the other hand, the TNF-inhibitory factor of the present invention does not bind to TNF and, if it does, this binding to TNF does not affect the TNF activity. Illustratively stated, when TNF is incubated together with the TNF-inhibitory protein of the present invention for 6 hours in a test tube and the resultant mixture is added to tumor cells, cytolysis of the cells is caused, that is, the TNF-inhibitory factor does not directly inhibit the TNF activity. However, when the TNF-inhibitory protein of the present invention is added to tumor cells 6 hours prior to the addition of TNF, the cytolytic activity of TNF for tumor cells is inhibited. The inhibition is observed even when the medium of tumor cells to which the TNF-inhibitory protein has been added is removed and a fresh medium is added before the addition of TNF. These facts suggest that the TNF-inhibitory protein of the present invention does not diminish the cytolytic activity of TNF by binding to TNF, in contrast to the conventional TNF-binding factor isolated from urine which binds to TNF to diminish the TNF activity. This TNF-Inhibitor described by others diminishes the cytolytic and/or cytostatic activity of TNF by binding to TNF. The complex of TNF*TNF-Inhibitor apparently cannot bind to TNF-Receptor (as does TNF without inhibitor). Thus, cells are not lysed by TNF (direct inhibition). TIP discovered by the present inventors interacts with cells (not with TNF) and as a result of this interaction such cells become resistant to the cytolytic and/or cytotoxic activity of TNF. The mechanism by which TIP induces resistance to the cytolytic and/or cytostatic activity of TNF is unknown. Theoretically, and without wishing to be bound by theory, TIP may induce changes in the number or affinity of TNF receptors and/or interfere with intracellular biochemical pathways (metabolic processes) activated by TNF (in TNF sensitive, untreated-with-TIP cells).

Furthermore, the properties of the TNF-inhibitory protein of the present invention differ from those of the above-mentioned TNF binding protein and TNF $\alpha$ inhibitor. Illustratively stated, the TNF binding protein binds to CM-Sepharose at pH 5.0 (J. Biol. Chem., 264' 11974–11980, 1989), but the TNF-inhibitory protein of the present invention does not. The TNF $\alpha$ inhibitor binds to DEAE-Sephadex at pH 8.0 (J. Biol. Chem., 264: 11966–11973, 1989), but the TNF-inhibitory protein of the present invention does not. In Eur. J. Haem., 41: 414–419, 1988, another inhibitory protein is reported and this reference discloses that the molecular weight of the inhibitory protein was reported to be 50 kDa. This molecular weight has been later corrected to 30 kDa (Eur. J. Haem., 42: 270–275, 1989). The molecular weight of the TNF-inhibitory protein of the present invention is 28 kDa as described above. Further, the activity of the TNF-inhibitory protein is not neutralized by an anti-TNF antibody, an anti-IL-1 antibody or an anti-IL-6 antibody.

The TNF-inhibitory protein of the present invention can be produced by culturing cells under appropriate conditions. Therefore, according to the present invention, there is also provided a method for producing the TNF-inhibitory protein, which comprises:

culturing cells in a nutrient medium containing no tumor necrosis factor;

culturing said cells in a medium containing TNF-inhibitory protein inducer, for example TNF or IL-1 or IL-6 or lymphotoxin and the like, to cause the cells to produce TNF-inhibitory protein; and isolating said TNF-inhibitory protein from said culture.

Examples of human-derived cells include cells of human fibroblast MLD or BG-9 or FS-4 cell lines, peripheral blood leukocytes and the like. The human-derived cells are cultured in a nutrient medium containing no TNF. As the nutrient medium, a minimum essential medium, such as RPMI 1640 medium, can be used. The culturing can generally be conducted at a temperature of, for example, about 37° C.

The TNF-inhibitory protein can be produced by culturing cells in the absence of TNF. However, when the cells are cultured in the presence of 10 units/ml to $10^4$ units/ml of TNF for about 2 to 24 hours, the amount of the TNF-inhibitory protein produced is increased 30 times or more over that of the TNF-inhibitory protein produced in the absence of TNF. As the medium containing TNF, the same medium as that used for obtaining the confluent cells can be used except that the above-mentioned TNF-inhibitory protein inducer is added. As the TNF, conventional TNF can be used. For example, human TNF produced according to the method described in European Patent Application Publication No. 0 158 286 can be used. The TNF-inhibitory protein produced by the cells accumulates inside the cells or outside the cells, i.e., in the culture medium so that a culture containing the TNF-inhibitory protein is obtained. Whether the TNF-inhibitory protein accumulates inside the cells or outside the cells depends upon the type of cell employed.

After completion of the culturing, the TNF-inhibitory protein is isolated from the culture. When the TNF-inhibitory protein accumulates inside the cells, cells are separated from the culture medium and disrupted, and a supernatant of the disrupted cells is obtained by centrifugation. The thus-obtained supernatant is subjected to purification. On the other hand, when the TNF-inhibitory protein accumulates outside the cells, i.e., in the culture medium, the culture medium is separated from the cells and subjected to purification. If desired, before subjecting the culture medium to purification, the culture medium may be centrifuged to remove cell debris remaining in the culture medium.

The purification may be conducted using customary techniques for purifying a protein, in combination. Examples of purification techniques include chromatography, such as gel filtration chromatography, ion-exchange chromatography, adsorption chromatography and reversed phase chromatography; ultrafiltration; electrophoresis; and the like.

The TNF-inhibitory protein of the present invention can advantageously be used as an antigen for producing a monoclonal or polyclonal antibody specific therefor, which antibody is useful for detecting a patient suffering from TNF-resistant cancer. The antibody is also useful for removing the TNF resistance of the cancer of a patient.

The use of the TNF-inhibitory protein of the present invention to prepare a monoclonal or polyclonal antibody may provide a novel approach to the therapy of acquired immune deficiency syndrome (AIDS). Manifestation of AIDS in patients with a latent infection of human immunodeficiency virus (hereinafter referred to as "HIV") appears after a long lag period and depends on enhanced expression of the HIV genome. TNF was found by others to amplify HIV replication in virus-infected cells. Thus, TNF antibodies or an antagonist which diminishes TNF activity may prevent TNF-induced amplification of the HIV genome. The opposite is also possible. Expression of the HIV genome was stimulated also by IL-1, a lymphokine which shares some biological activities with TNF, including (as discovered by the present inventors) stimulation of TNF Inhibitory Protein. When TNF was added to cells together with interferon-gamma (hereinafter referred to as "IFN-gamma"), it greatly reduced their susceptibility to HIV and suppressed production of HIV mRNA and core protein p24. The present inventors found that IFN-gamma reduces the ability of TNF to enhance TNF Inhibitory Protein in both human fibroblasts and peripheral blood leukocytes (hereinafter referred to as PBL). Thus, it may be that not TNF nor IL-1, but TIP induced by TNF and/or IL-1 amplifies the expression of HIV and mediates some other processes currently believed to be due to TNF or IL-1. If so, then, not TNF antibodies (TIP may be stimulated by other lymphokines) or TIP, but antibodies to TNF Inhibitory Protein may provide a novel approach to combatting AIDS.

The TNF-inhibitory protein of the present invention can also advantageously be used as a modulator for appropriately controlling various activities of TNF.

The present inventors have discovered that human fibroblasts, PBL, as well as some established tumor cell lines can be stimulated to enhance production of TNF Inhibitory Protein which, when added to tumor cell lines sensitive to TNF-induced lysis renders them resistant. TNF-mediated processes however are not limited to lysis of some transformed cells. TNF plays an important role in the host defense system, graft-versus-host disease, differentiation of B cells, regulation of expression of HIV, and numerous other processes. Thus it is reasonable to expect that TIP may have an effect on these processes as well. Without wishing to be bound by theory, it is believed that TIP and/or its antibody can be used to reduce tumor cell resistance against TNF-mediated lysis, to inhibit TNF induced amplification of the HIV genome, to diminish severity of graft-versus-host disease, to prevent TNF/IL-1 mediated lethal effects of endotoxin, etc. They may also be used for patient selection for TNF therapy and for studies of the cytokine network.

Further, the TNF-inhibitory protein of the present invention can be used for the management of organ or tissue transplants, particularly for reducing the rate of rejection of organ transplants.

Graft-versus-host reactions following bone marrow transplantation (hereinafter referred to as "BMT") may result in graft failure, a fatal complication, usually leading to the death of the patient. A successful graft may evoke graft-versus-host disease (hereinafter referred to as GVHD), a complication that may carry up to 50% mortality. Depletion of T-cells from bone marrow, or use of immunosuppressive drugs significantly reduces the incidence and severity of GVHD but frequently results in an increased incidence of graft failure, infection, and recurrent leukemia. An increased level of TNF has been observed during GVHD, and it was suggested that TNF may be responsible for the induction and severity of GVHD. Interleukin-2 (hereinafter referred to as "IL-2") significantly increased production of TNF by lymphocytes obtained from patients after T cell-depleting BMT. Antibody to TNF significantly decreased mortality after BMT, prevented skin and gut lesions and other effects of the acute phase of GVHD. For this reason, it is expected that antibodies or other TNF antagonists may have potential use for the management of organ or tissue transplants.

DESCRIPTION OF PREFERRED EMBODIMENTS

The present invention will now be described in detail with reference to the following Examples, which should not be construed as limiting the scope of the present invention.

In the following Examples, the cell maintenance was conducted as follows, using the following culture media:

MLD cells: The cells were maintained routinely in a minimum essential medium (hereinafter referred to as "MEM") or RPMI 1640 medium supplemented with 2% fetal bovine serum (hereinafter referred to as "FBS"), 8% bovine calf serum (hereinafter referred to as "BCS") and 0.1 mg/ml gentamycin.

RT4 cells and A2780 cells: The cells were grown in RPMI 1640 medium supplemented with 10% FBS and 0.1 mg/ml gentamycin.

L929 cells: The cells were kept in RPMI 1640 medium supplemented with 5% FBS and 0.1 mg/ml gentamycin.

Further, in the following Examples, the assay for cytotoxicity and the TNF-inhibitory activity of the TNF-inhibitory protein were conducted by the following methods.

(1) Assay for cytotoxicity:

L929 cells (American Type Culture Collection CCL1) are seeded in each well of 96-well microtiter plates at a density of $3 \times 10^4$ cells/well. After the plates are incubated for 24 hours, samples in serial dilutions containing the TNF-inhibitory protein are individually added to respective wells and, immediately thereafter, cycloheximide (CHI) is added so that the final concentration becomes 0.05 mg/ml. The cells are incubated at 37° C. for 16 hours and then fixed with 10% (v/v) formalin and stained with 0.05 %(w/v) methylene blue. The cells in each well were washed with water and the dye (methylene blue) remaining in the cells is eluted with 50% (v/v) ethanol. The absorbance of the eluate in each well is measured at 650 nm using a Bio-Tek Microplate Autoreader EL311 (manufactured and sold by Bio-Tek Instruments Inc., Winooski, Vt.). The absorbance is proportional to the number of viable L929 cells. Therefore, the cytotoxic activity of each sample for L929 cells is evaluated from the absorbance.

(2) Assay for TNF-inhibitory activity:

MLD cells are seeded in each well of 96-well microtiter plates containing a growth medium at a density of $3 \times 10^4$ cells/well. After incubating the plates for 24 hours, the growth medium for the cells is aspirated and replaced with RPMI 1640 medium containing 2% BCS. Samples in serial dilutions containing the TNF-inhibitory protein are individually added to respective wells, and the plates are incubated for 12 hours. Then, the medium is removed from the well while leaving the cells in the well, and the cells are treated with TNF (1,000 units/ml) and CHI (0.1 mg/ml) dissolved in RPMI 1640 containing 2% BCS. The TNF used has a specific activity of $2.3 \times 10^6$ units/mg as measured by the method of Yamazaki et al., Japan J. Med. Sci.Biol., 39, 105 (1986). Cells are incubated at 37° C. for 16 hours, and fixed with 10% formalin and stained with 0.05% (w/v) crystal violet. The dye (crystal violet) staining the cells is eluted with 50% ethanol and its absorbance is measured at 600 nm using the above-mentioned Bio-Tek Microplate Autoreader EL 311.

The amount of the TNF-inhibitory protein is expressed in terms of units. Unit means a quantity of TNF-inhibitory protein which protects 50% of $3 \times 10^4$ of the MLD cells from cytolytic activity of 1,000 units/ml TNF and 0.1 mg/ml CHI, that is, a quantity by which 50% of $3 \times 10^4$ cells remain viable after such treatment. Cell viability is calculated as the ratio of the number of viable cells to the number of cells seeded and is proportional to absorbance. In calculation, the absorbance obtained with respect to the cells incubated together with CHI (0.1 mg/ml) only is interpreted as "100% cell viability", while the absorbance obtained with respect to the cells incubated together with 1,000 units/ml TNF and 0.1 mg/ml CHI is interpreted as "0% cell viability".

EXAMPLE 1

Step 1 (Preparation of cells)

Cells of a human fibroblast cell line MLD (e.g., from the foreskin of new-born babies such as MLD cells provided by Dr. J. S. Horoszewicz) were grown in an MEM containing 10% FBS in tissue culture dishes ($100 \times 20$ mm style, manufactured and sold by Becton Dickinson Labware, Lincoln Park, U.S.A.) to obtain confluent cells. $3 \times 10^9$ cells of the thus-obtained confluent cells were collected and cultured in an MEM containing 100 units/ml of TNF having a specific activity of $2.3 \times 10^6$ units/mg which had been prepared in accordance with the method described in European Patent Application Publication No. 0,158,286, the disclosure in which is incorporated herein by reference. The culturing was conducted for 8 hours to stimulate the cells, causing the cells to produce the TNF-inhibitory protein. The confluent cells were washed with a phosphate-buffered saline (hereinafter referred to as "PBS") three times then frozen and detached from the tissue culture dishes by means of a rubber scraper, and suspended in 0.9 liter of PBS. The resultant suspension was sonicated and centrifuged at $100,000 \times g$ for 1 hour to obtain a supernatant containing the TNF-inhibitory protein. From 0.9 liter of the supernatant, the TNF-inhibitory protein was purified in the manner described below.

Step 2 (Purification of TNF-inhibitory protein)

0.9 Liter of the supernatant was mixed with 0.1 liter of 1 M sodium acetate (pH 4.9) and poured into a beaker containing 100 ml of controlled pore glass (CPG.10, 120-200 mesh, manufactured and sold by Serva Feinbiochemica, Heidelberg, West Germany) previously equilibrated with 0.1 M sodium acetate (pH 5.0) and gently mixed for 1 hour. The liquid was removed from the mixture by suction. The resultant controlled pore glass was packed in a K50/30 column (manufactured and sold by Pharmacia LKB Biotechnology, Piscataway, U.S.A.). A fraction having TNF-inhibitory activity was eluted out from the column with 3 bed volumes (300 ml) of a PBS containing 0.5 M tetramethylammonium chloride (pH 7.4) at a flow rate of 15 ml/cm²/hour (300 ml/hour). Solid sodium chloride was added to the fraction so that the resultant solution had a sodium chloride concentration of 5 M. The fraction was then adjusted to pH 7.4 with 5 N NaOH and applied to a K-26/40 column (manufactured and sold by Pharmacia LKB Biotechnology, U.S.A.) packed with 20 ml of Phenyl-Sepharose CL-4B, which had been equilibrated with 0.02 M phosphate buffer (pH 7.4) containing 0.5 M tetramethylammonium chloride and 5 M NaCl (equilibration buffer). The application of the fraction to the column was conducted at a flow rate of 10 ml/cm²/hour. The column was washed with 3 bed volumes of the above-mentioned equilibration buffer. Then, the column was connected through a tubing to a K16/20 column packed with $Cu^{2+}$-chelating Sepharose 6B (manufactured and sold by Pharmacia LKB Biotechnology, U.S.A. and prepared as described by Sulkowski, Trends in Biotechnology 3: 1-7, 1985), which column had been equilibrated with PBS (pH 7.4). The fraction having TNF-inhibitory activity was transferred from the Phenyl-Sepharose CL-4B column to the $Cu^{2+}$-chelating Sepharose 6B column by eluting the fraction in the Phenyl-Sepharose column with PBS (pH 7.4) at a flow rate of 10 ml/cm²/hour. To complete the transfer, 100 ml of PBS (5 bed volumes of the Phenyl-Sepharose column) was required. The $Cu^{2+}$-chelating Sepharose column was washed with 3 bed volumes (15 ml) of PBS (pH 7.4) and connected through a tubing to a K9/15 column packed with 2 ml of $Fe^{3+}$-chelating Fast Flow Sepharose (manufactured and sold by Pharmacia LKB Biotechnology, U.S.A. and prepared as described by Sulkowski, Trends in Biotechnology 3: 1–7, 1985), which had been equilibrated with a solution containing 0.1 M sodium acetate and 1M NaCl (pH 4.0). The fraction having TNF-inhibitory activity was displaced from the $Cu^{2+}$-chelating Sepharose column and loaded onto the $Fe^{3+}$-chelating Sepharose column using 5 bed volumes (25 ml) of a sodium acetate buffer containing 0.1 M sodium acetate and 1M NaCl (pH 4.0). The loading of the fraction onto the $Fe^{3+}$-chelating Sepharose column was conducted at a flow rate of 10 ml/cm²/hour. Then, the $Fe^{3+}$-chelating Sepharose column was washed with 5 bed volumes (10 ml) of the above-mentioned sodium acetate buffer, and connected through a tubing to a 2 ml Poly-Prep disposable polypropylene column (manufactured and sold by Bio-Rad Laboratories, U.S.A.) packed with 1 ml of DEAE-Sepharose, which had been equilibrated with 0.1 M Tris-HCl buffer (pH 10.0). The TNF-inhibitory protein adsorbed on the $Fe^{3+}$-chelating Sepharose column was eluted from the column with 10 ml of 0.1 M Tris-HCl buffer (pH 10.0) at a flow rate of 5 ml/cm²/hour, thereby loading the factor onto the DEAE-Sepharose column. The DEAE-Sepharose column was washed with 5 bed volumes of the above-mentioned Tris-HCl buffer. The TNF-inhibitory protein was eluted from the column with 15 ml of 0.1 M sodium acetate containing 0.15 M NaCl (pH 6.0) under gravity to obtain a fraction containing the TNF-inhibitory protein. The thus obtained fraction was concentrated using a Multiple-Micro-ProdiCon model 310 (manufactured and sold by Bio-Molecular Dynamics, Beaverton, U.S.A.), to thereby obtain a concentrate containing the TNF-inhibitory protein.

Step 3 (Characterization of TNF-inhibitory protein)

An aliquot of the concentrate obtained in Step 2 was subjected to 15 % sodium dodecyl sulfate-polyacrylamide gel electrophoresis (SDS-PAGE). The resultant gel was stained with silver whereupon two bands were observed on the gel, that is, a main band corresponding to a molecular weight of 28 kDa and a second band corresponding to a molecular weight of 33.4 kDa. From the gel, approximately 100 ng of a 28 kDa protein was isolated by electroelution using Elutrap System (manufactured and sold by Schleicher and Schuell, Keene, U.S.A.) according to the method described in the manual provided with the System.

The isolated 28 kDa protein was examined with respect to the activity of inhibiting the cytolytic and/or cytostatic activity of TNF for cells of human fibroblast cell line MLD and the cytotoxic activity for L929 cells according to the methods described above. Results show that the protein protected the MLD cells from the cytolytic activity of TNF, and did not lyse L929 cells.

Another aliquot of the concentrate was serially diluted, and the obtained dilutions were individually incubated for 2 hours, respectively, with 50 µl of a solution containing 1,000 units/ml of anti-TNF monochlonal antibody obtained by the method described in Japanese Patent Application Laid-Open Specification No. 61-63698, with 50 µl of a solution containing 1,000 units/ml of anti-IL-1 polyclonal antibody (manufactured and sold by Genzyme, U.S.A., lot #01737), with 50 µl of a solution containing 1,000 units/ml of anti IL-6 polyclonal antibody (manufactured and sold by Genzyme, U.S.A., lot #B8112), and with a mixture of the above-mentioned solutions each in an amount of 16.7 µl. Each of the resultant incubation solutions was mixed with 200 µl of Protein A Sepharose CL-4B (manufactured and sold by Pharmacia Fine Chemicals AB, Sweden), followed by incubation for 1 hour. Then, the mixture was centrifuged to obtain a supernatant. The supernatant was used for assay of the activity of inhibiting the TNF activity for MLD cells by the method described above. Results show that the TNF-inhibitory activity of the 28 kDa protein was not affected by the incubation with each of the anti-TNF monoclonal antibody, anti-IL-1 polyclonal antibody, anti-IL-6 polyclonal antibody or mixture thereof.

In addition, the TNF-inhibitory protein was incubated in a test tube together with TNF for 6 hours. The resultant mixture was added to MLD cells maintained in the microtiter plates, and the cytolytic activity of TNF for the MLD cells was examined. Results show that the cytolytic activity of TNF was not affected. This means that the TNF-inhibitory protein does not directly inhibit the cytolytic activity of TNF.

The above-described data suggest that the TNF-inhibitory protein of the present invention does not diminish the cytolytic activity of TNF by binding to TNF, differing from the conventional TNF-binding factor isolated from urine, and that the TNF-inhibitory protein of the present invention may induce some metabolic processes to decrease the cytolytic activity of TNF.

EXAMPLE 2

Step 1 (Preparation of a supernatant of culture) Peripheral blood leukocytes (PBL) were concentrated from 250 ml of donor blood and isolated using Ficoll-Pacque (manufactured and sold by Pharmacia, Sweden), and suspended in 50 ml of RPMI 1640 medium containing 10% FBS and TNF (100 units/ml) prepared by the method described above. After the incubation of the mixture at 37° C. for 8 hours, the cells were collected from the culture by centrifugation at 400×g for 10 minutes to separate the culture into a spent medium and PBL. The supernatant was removed, and the PBL were collected and washed with PBS and centrifuged. The washing and centrifugation were conducted three times in total. The resultant PBL were suspended in RPMI 1640 medium containing 10% FBS at a cell concentration of $3 \times 10^6$ cells/ml and incubated at 37° C. for 24 hours. The resultant conditioned medium as such (namely, not a cellular homogenate as in Example 1 in which MLD cells were used) was subjected to purification of TNF-inhibitory protein, as follows.

Step 2 (Purification of TNF-inhibitory protein)

The conditioned medium was taken off from the medium, and filtered off through a 8 µm-thick membrane filter to remove a cellular debris remaining in the conditioned medium. The resultant supernatant was subjected to purification as described below. All of the following purification operations were conducted at 4° C. 2.7 Liter of the medium was acidified to pH 5.0 with 0.3 liter of 1 M sodium acetate (pH 4.9) in a vol/vol proportion of 9 (medium) :1 (sodium acetate). The acidified material was distributed in plastic flasks containing 30 ml of controlled-pore glass (CPG sold by Serva Feinbiochemica) (1 ml of CPG/100 ml of acidified material) previously equilibrated with 0.1 M sodium acetate (pH 5.0). After gently mixing for 1 hour, the liquid was removed from the mixture by suction to obtain the CPG. The CPG was packed in a K26/40 column (manufactured and sold by Pharmacia LKB Biotechnology, Piscatway, U.S.A.). The column was successively washed with 6 bed volumes (180 ml) of 0.1 M sodium acetate (pH 5.0), and 6 bed volumes (180 ml) of 0.02 M sodium phosphate (pH 7.4). The elution was conducted using as an eluant a linear gradient of tetramethylammonium chloride (from 0 to 0.5 M) in PBS (pH 7.4) at a flow rate of 30 ml/cm2/hr (150 ml/hr), and 4 ml-fractions were collected. The volume of the eluant used was equal to 10 bed volumes (300 ml). Fraction Nos. 17 to 49 exhibited TNF-inhibitory activity. These fractions were combined. Solid sodium chloride was added to the combined fraction to a final concentration of 5 M. The resultant fraction was then applied to a K-16/20 column (Pharmacia LKB Biotechnology, U.S.A.) packed with 15 ml of Phenyl Sepharose CL 6B (Pharmacia LKB) which had been equilibrated with 5 M aqueous NaCl solution. The flow rate during the application of the fraction to the column was 25 ml/cm$^2$/hr (50 ml/hr). The column was then washed with 6 bed volumes (90 ml) of 5 M NaCl and 6 bed volumes (90 ml) of 0.02 M phosphate buffer (hereinafter referred to as "PB") containing 3 M NaCl (pH 7.4). Then, the elution was conducted with 200 ml of a linear gradient of NaCl (from 3 M to 0.15 M) in PB at a flow rate of 50 ml/cm$^2$/hr (100 ml/hr) and 4 ml-fractions were collected. Fraction Nos. 9 to 30 exhibited TNF-inhibitory activity. These fractions were combined and mixed with 100 mM imidazole to a final imidazole concentration of 1 mM. The resultant solution was adjusted to pH 7.4 with 1 M NaOH and applied to a K-16/20 column packed with 5 ml of $Cu^{2+}$-imidazole-Sepharose at a flow rate of 15 ml/cm$^2$/hr (30 ml/hr). The $Cu^{2+}$-imidazole-Sepharose acked column had been prepared as follows. A K-16/20 column packed with Chelate Sepharose 6B (manufactured and sold by Pharmacia LKB Biotechnology, U.S.A.) was washed with a solution of $CuSO_4$ at pH 4. After the equilibration of the column with PBS, the resultant $Cu^{2+}$-Sepharose contained in the column was saturated with 6 bed volumes (25 ml) of 25 mM imidazole in PBS, and equilibrated with 1 mM imidazole in PBS.

After washing the column with 6 bed volumes (30 ml) of 1 mM imidazole in PBS, the elution was conducted using as an eluant a linear gradient of imidazole (from 1 mM to 25 mM) and 2 ml-fractions were collected at a flow rate of 25 ml/cm$^2$/hr (50 ml/hr). Total volume of the eluant was 100 ml (20 bed volumes). Fraction Nos. 6 to 20 exhibited TNF-inhibitory activity. These fractions were combined and concentrated to 1 ml using an Amicon cell, model 52, equipped with YM 10 membrane (manufactured and sold by Amicon, U.S.A.). The concentrate was applied to a K-16/100 column (Pharmacia LKB Biotechnology, U.S.A.) packed with Sephacryl S-100 HR (Pharmacia LKB Biotechnology, U S A ) to conduct gel filtration at a flow rate of 5 ml/cm$^2$/hr (10 ml/hr) and 2 ml-fractions were collected. Fraction Nos. 46 to 52 exhibited TNF-inhibitory activity. These fractions were pooled and applied to $Cu^{2+}$-chelating Sepharose (5 ml) (manufactured and sold by Pharmacia LKB Biotechnology, prepared as described by Sulkowski, Trends in Biotechnology 3: 1–7, 1985) packed into a K 16/20 (Pharmacia LKB Biotechnology) column. The column was washed successively with 6 bed volumes of PBS (30 ml), 6 bed volumes (30 ml) of 0.1 M sodium acetate (pH 5.0) and 6 bed volumes of 0.1 M sodium acetate (pH 5.0) containing 0.15 M NaCl, and the elution was conducted with a linear pH gradient of sodium acetate (from pH 6.0 to pH 4.0) containing 1 M NaCl at a flow rate of 15 ml/cm$^2$/hr (30 ml/hr). Two ml-fractions were collected as eluates. Fraction Nos. 14 to 28 (pH 4.7-4.0) exhibited TNF-inhibitory activity. These fractions were pooled and applied to a K-9/15 column (Pharmacia LKB Biotechnology, U.S.A.) packed with 2 ml of $Fe^{3+}$ chelating Sepharose Fast Flow (manufactured and sold by Pharmacia LKB Biotechnology, prepared as described by Sulkowski, Trends in Biotechnology 3: 1–7, 1985) and equilibrated with 0.1 M sodium acetate (pH 4) containing 1 M NaCl. The column was washed successively with 6 bed volumes (12 ml) of 0.1 M sodium acetate (pH 4) containing 1 M NaCl, 6 bed volumes (12 ml) of 0.1 M sodium acetate (pH 6). TNF-inhibitory protein was eluted out from the column with 6 bed volumes (12 ml) of 0.1 M Tris buffer (pH 10). The above-mentioned operations, that is, the application of the sample to the K-9/15 column, the washing, and the elution, were conducted at a flow rate 50 ml/cm$^2$/hr (32 ml/hr). The resultant eluate was applied to a K-9/15 column (Pharmacia LKB Biotechnology, U.S.A.) packed with 2 ml of DEAE-Sepharose CL-6B. The column was washed successively with 6 bed volumes of 0.1 M Tris buffer (pH 10), 6 bed volumes of 0.1 M Tris buffer (pH 10) containing 0.05 M NaCl, and 6 bed volumes of 0.1 M sodium acetate (pH 6.0). The elution was conducted with 20 bed volumes (40 ml) of a linear gradient of NaCl (from 0 to 150 mM) in 0.1 M sodium acetate (pH 6) and 2 ml fractions were collected. Fraction Nos. 10 to 15 exhibited TNF-inhibitory activity. These fractions were pooled and applied to a K-9/15 column (Pharmacia LKB Biotechnology, U.S.A.) packed with 2 ml of hydroxylapatite (manufactured and sold by BioRad, Richmond, California) equilibrated with 0.1 M sodium acetate (pH 6) containing 0.15 M NaCl. The column was washed successively with 6 bed volumes of 0.1 M sodium acetate (pH 6) containing 0.15 M NaCl, 6 bed volumes of 1 M NaCl, 6 bed volumes of 0.001 M sodium phosphate (pH 6.8). A fraction containing TNF-inhibitory protein was eluted out with 6 bed volumes of 0.1 M sodium phosphate (pH 6.8). The above-mentioned operations, that is, the application of the sample to the K-9/15 column, the washing, and the elution, were conducted at a flow rate 50 ml/cm$^2$/hr (32 ml/hr). The TNF-inhibitory protein in the fraction was concentrated using a Multiple-Micro-Prodicon Model 310 (Bio Molecular Dynamics, Beaverton, U.S.A.) to obtain a concentrate of TNF-inhibitory protein.

Step 3 (Characterization of TNF-inhibitory protein)

The concentrate obtained in Step 2 was subjected to electrophoresis on 15% SDS-polyacrylamide gel and staining with silver. As a result, 4 protein bands corresponding to molecular weights of 37 kDa, 28 kDa, 18 kDa and 9 to 13 kDa were found. The protein of 28 kDa was isolated from the gel in the same manner as in Step 3 of Example 1 to obtain about 80 ng of the TNF-inhibitory protein.

The activity of the TNF-inhibitory protein was examined by the same method as in Step 3 of Example 1. Results show that the TNF-inhibitory activity of the TNF-inhibitory protein was not affected by the incubation with any of the anti-TNF monoclonal antibody, anti-IL-1 polyclonal antibody, anti-IL-6 polyclonal antibody and mixtures thereof.

EXAMPLE 3

(Inhibitory activity of TNF-inhibitory protein against lysis of TNF-sensitive cell lines RT4 and A2780 by TNF).

The ability of TNF-inhibitory protein to prevent the cytolytic activity of TNF was assayed using TNF-sensitive tumor cells (human bladder carcinoma cell line RT4 (ATTC HTB 2) and human ovarian carcinoma cell line A2780 (donated by Dr. Y. Otsuka, Asahi Chemical Industry Co., Ltd.).

The RT4 cells and A2780 cells each were individually seeded in the medium described above charged in 96 well microplates at a density of $1 \times 10^3$ cells/well. After incubation for 24 hours, the medium in each well was removed and replaced with a fresh medium containing TNF-inhibitory protein obtained in Example 1 at a concentration of 100 units/ml. After the incubation for 24 hours, TNF was added to wells at different concentrations of 1, 10, 100, 1,000, 10,000 units/ml, followed by culturing. Five days later, the cell growth in each well was determined by the MTT assay of Danizot and Lang (J. Immunol. Meth., 89: 271-277, 1986). Illustratively stated, the culture medium in the well was removed while leaving the cells in the well by inverting, flicking and blotting the microplate. To each well was added 100 μl of RPMI 1640 medium containing 1 mg/ml of 3-(4,5-dimethylthiazol-2-yl)-2,5 diphenyl tetrazolium bromide (MTT). The plate was incubated for 4 hours at 37° C. After completion of the incubation, the MTT remaining untransformed was carefully removed from each well and propanol (150 μl) was added to each well. The plate was shaken and the absorbance of each well was measured at 570 nm using a Bio-Tek Microplate Autoreader model 310 (manufactured and sold by Bio-Tek Instruments Inc.; Winooski, Vt.).

As a control, substantially the same procedure as described above was repeated except that TNF was not added to each well.

The cell growth was expressed in terms of a ratio (%) of the cell number of the TNF-added well to the cell number of the control well. The assay was conducted 3 times with respect to each of the TNF concentrations and TNF-inhibitory protein concentrations, and the mean and standard deviation of the cell growth were calculated.

Figure 2:
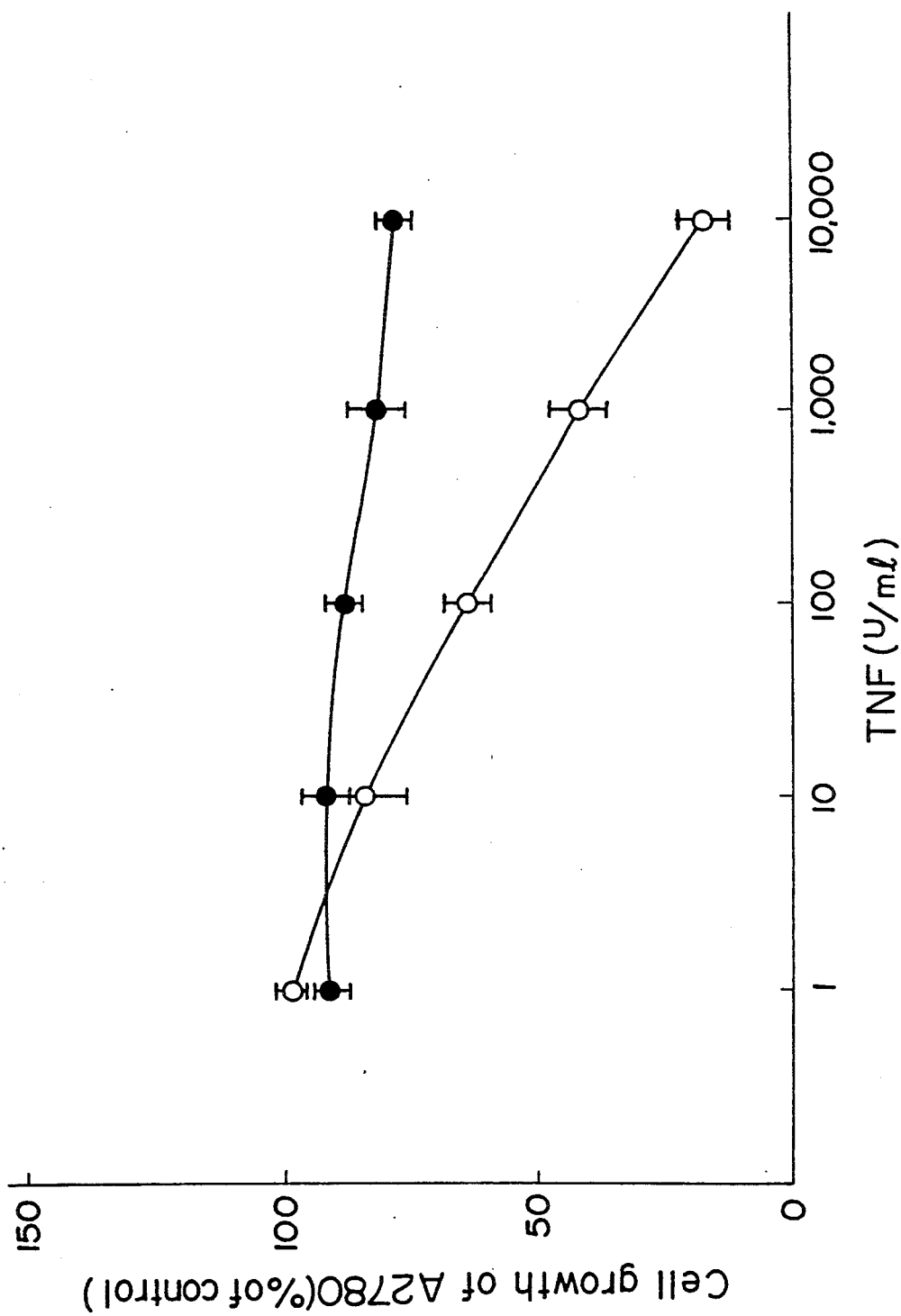
FIG. 2 is a graph showing the relationship between the concentration of TNF and the growth of A2780 cells (human ovarian carcinoma cell line) treated with the TNF-inhibitory protein (shown by the symbol "●—●", in comparison with the corresponding relationship for the case where the cells are not so treated (shown by the symbol "O—O").

Results are shown in FIGS. 1 and 2. In FIGS. 1 and 2, the symbol indicates the results obtained in respect of the TNF-inhibitory protein concentration of 0 unit/ml, and the symbol indicates the results obtained in respect of the protein concentration of 100 units/ml.

As is apparent from the results, the TNF-inhibitory protein of the present invention rendered resistant to TNF the TNF-sensitive cells RT4 and A2780 to thereby inhibit the cytolytic activity of TNF for the cells.

What is claimed:

1. A purified and isolated TNF-inhibitory protein having:
   (a) a molecular weight of 28 kilodaltons;
   (b) no activity of directly inhibiting the activity of tumor necrosis factor; and
   (c) an activity of rendering resistant to tumor necrosis factor a tumor necrosis factor-sensitive cell to thereby inhibit the cytolytic and/or cytostatic activity of said tumor necrosis factor for the tumor necrosis factor-sensitive cell in the presence of cycloheximide,
   said TNF-inhibitory protein being substantially free of proteins and cell components with which it naturally occurs.

2. The TNF-inhibitory protein according to claim 1, wherein said tumor necrosis factor-sensitive cell is a cell of human fibroblast cell line MLD.

3. The TNF-inhibitory protein according to claim 1, wherein said tumor necrosis factor-sensitive cell is a cell of human bladder transitional cell papilloma line RT4.

4. The TNF-inhibitory protein according to claim 1, wherein said tumor necrosis factor-sensitive cell is a cell of human ovarian carcinoma cell line A2780.

5. A method for producing a TNF-inhibitory protein, which comprises:
   culturing human-derived cells in a medium containing TNF-inhibitory protein inducer to stimulate production of a TNF-inhibitory protein in the cultured cells, said TNF-inhibitory protein having:
   (a) a molecular weight of 28 kilodaltons,
   (b) no activity of directly inhibiting the activity of tumor necrosis factor, and
   (c) an activity of rendering resistant to tumor necrosis factor a tumor necrosis factor-sensitive cell to thereby inhibit the cytolytic and/or cytostatic activity of said tumor nexrosis factor for the tumor necrosis factor-sensitive cell in the presence of cycloheximide; and
   isolating said TNF-inhibitory protein from said culture, said isolated TNF-inhibitory protein being substantially free of proteins and cell components with which it naturally occurs.

6. The method according to claim 5, wherein said human-derived cells are cells of human fibroblast MLD.

7. The method according to claim 5, wherein said human-derived cells are cells of BG-9 cell line.

8. The method according to claim 5, wherein said human-derived cells are cells of FS-4 cell line.

9. The method according to claim 5, wherein said human-derived cells are cells of peripheral blood leucocytes.

10. The method according to claim 5, wherein said TNF-inhibitory protein inducer is tumor necrosis factor.

11. The method according to claim 5, wherein said TNF-inhibitory protein inducer is IL-1.

12. The method according to claim 5, wherein said TNF-inhibitory protein inducer is IL-6.

* * * * *